(12) United States Patent
Tetreault et al.

(10) Patent No.: US 6,652,559 B1
(45) Date of Patent: Nov. 25, 2003

(54) WOUND CLOSURE SYSTEM

(75) Inventors: Stephane Tetreault, Boucherville (CA); Simon Phaneuf, Longueuil (CA); Mahmed Benchabane, Joliette (CA)

(73) Assignee: Advanced Terapeutic Technologies AT² Inc., Quebec (CA)

( * ) Notice: Subject to any disclaimer, the term of this patent is extended or adjusted under 35 U.S.C. 154(b) by 0 days.

(21) Appl. No.: 09/914,038

(22) PCT Filed: Feb. 16, 2000

(86) PCT No.: PCT/CA00/00163
§ 371 (c)(1),
(2), (4) Date: Aug. 22, 2001

(87) PCT Pub. No.: WO00/49983
PCT Pub. Date: Aug. 31, 2000

(30) Foreign Application Priority Data

Feb. 23, 1999 (CA) .............................................. 2262408

(51) Int. Cl.⁷ .............................................. A61B 17/08
(52) U.S. Cl. ...................................... 606/214; 606/213
(58) Field of Search ........................ 602/48, 54, 41–56; 606/213–216

(56) References Cited

U.S. PATENT DOCUMENTS

| 4,161,176 A | 7/1979 | Harris, II et al. ............ 128/155 |
| 4,360,020 A | 11/1982 | Hitchcock, Jr. et al. ..... 128/269 |
| 4,498,655 A | 2/1985 | Tendler ...................... 248/467 |
| 4,600,001 A | 7/1986 | Gilman ........................ 128/156 |
| 5,259,835 A | 11/1993 | Clark et al. .................... 602/48 |
| 5,840,052 A | * 11/1998 | Johns .......................... 602/54 |

FOREIGN PATENT DOCUMENTS

| EP | 0 300 815 | 1/1989 |
| EP | 0 641 553 | 3/1995 |
| EP | 0 700 674 | 3/1996 |
| EP | 0 870 488 | 10/1998 |

* cited by examiner

*Primary Examiner*—Weilun Lo
*Assistant Examiner*—Linh Truong
(74) *Attorney, Agent, or Firm*—Foley & Lardner

(57) ABSTRACT

A wound closure system (10) for closing a wound on a patient comprises an elongated flexible backing strip (12) having a length and width sufficient to secure facing edges of the wound in close juxtaposition to one another, the backing strip comprising a first portion disposed between the ends and adapted to overlie the facing edges of the wound, and second and third portions disposed on either side of the first portion and each provided with a predetermined number of spaced-apart apertures extending through the backing strip from one surface thereof to the other; and a first pressure-sensitive adhesive (18) coated on at least part of the first surface of the backing strip (12) including the second and third portions thereof, to adhere the backing strip to the patient with the facing edges of the wound being in close juxtaposition. The wound closure system of the invention further includes a flowable, moisture-curable surgical adhesive (28) for application into the apertures to strengthen the adhesion of the second and third portions of the backing strip to the patient.

19 Claims, 4 Drawing Sheets

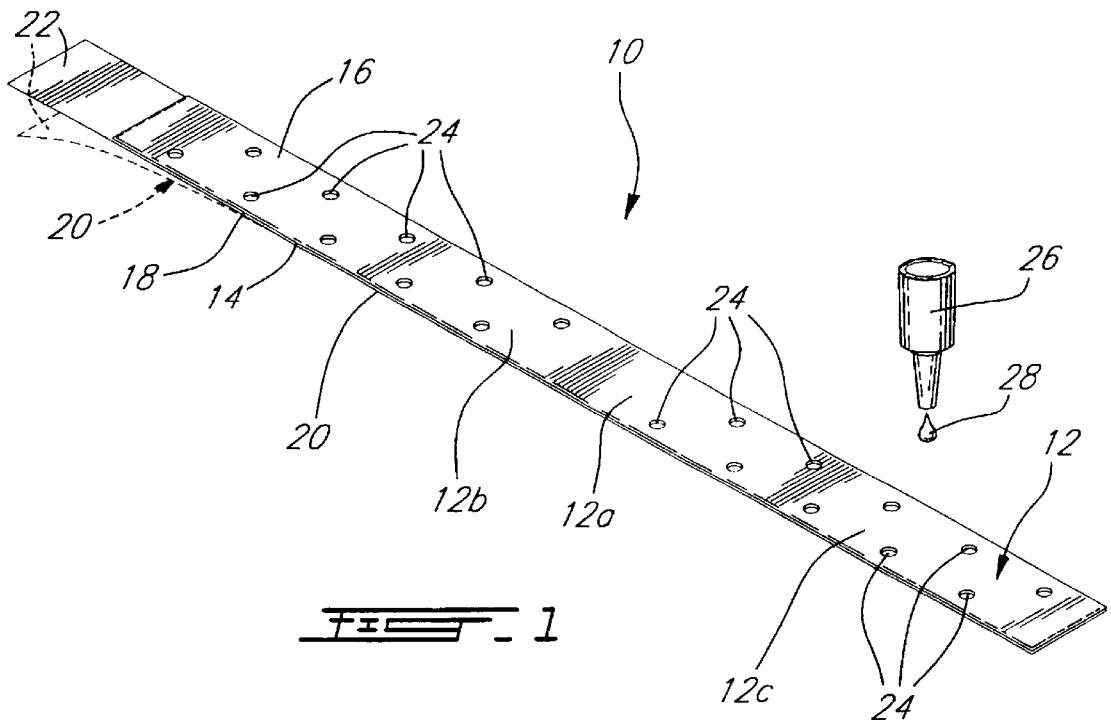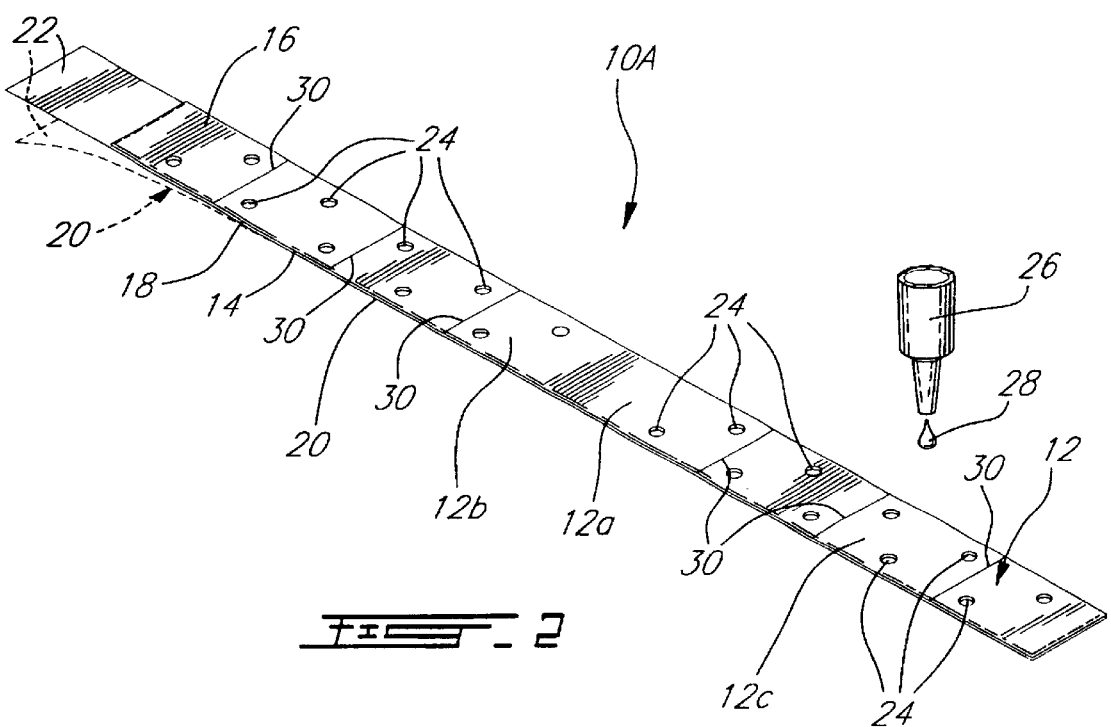

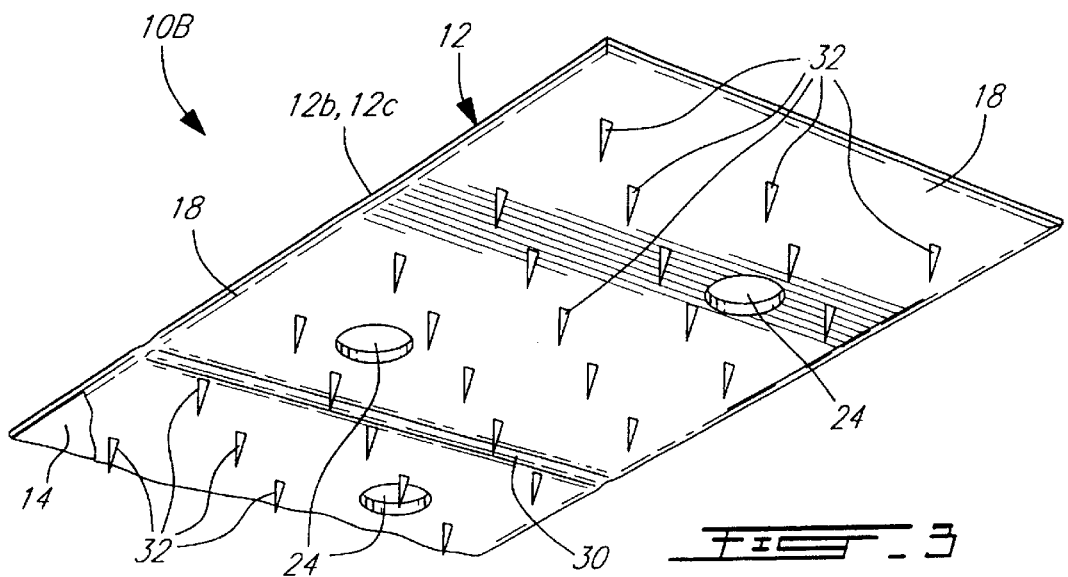
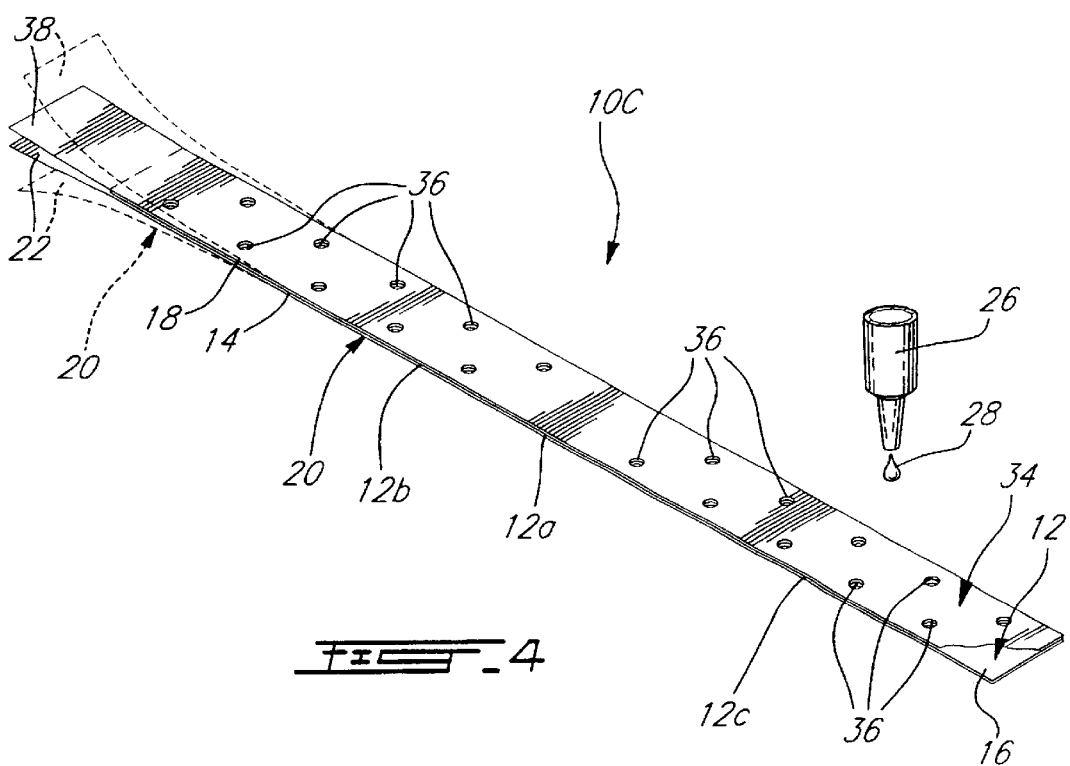

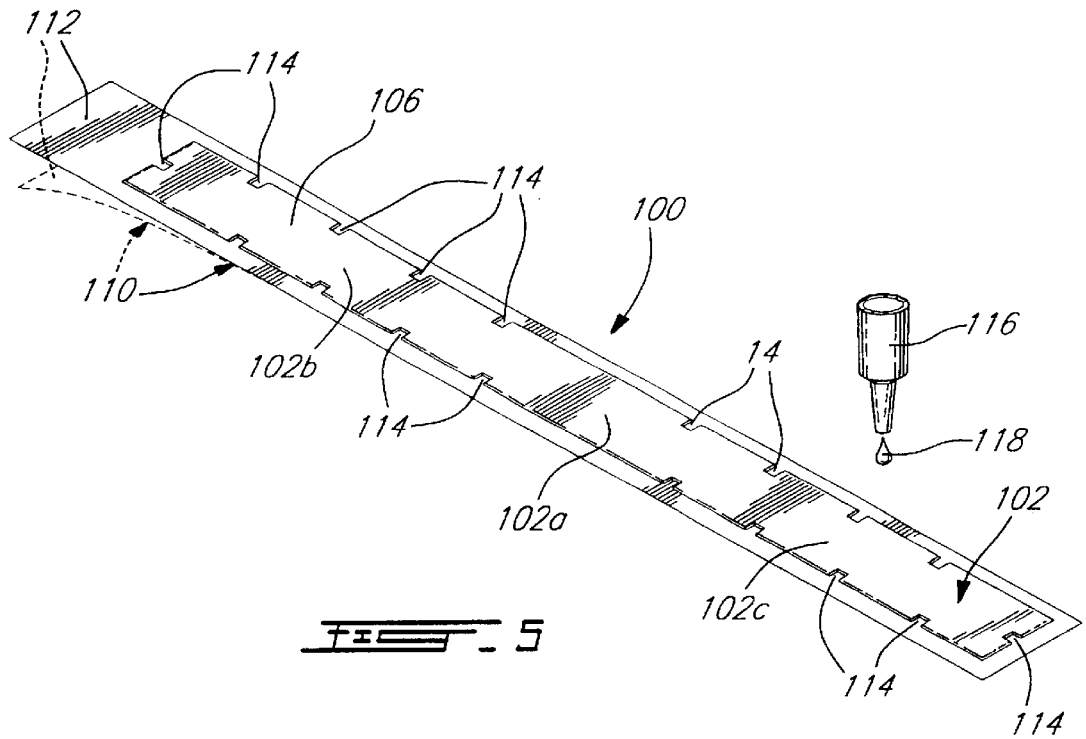
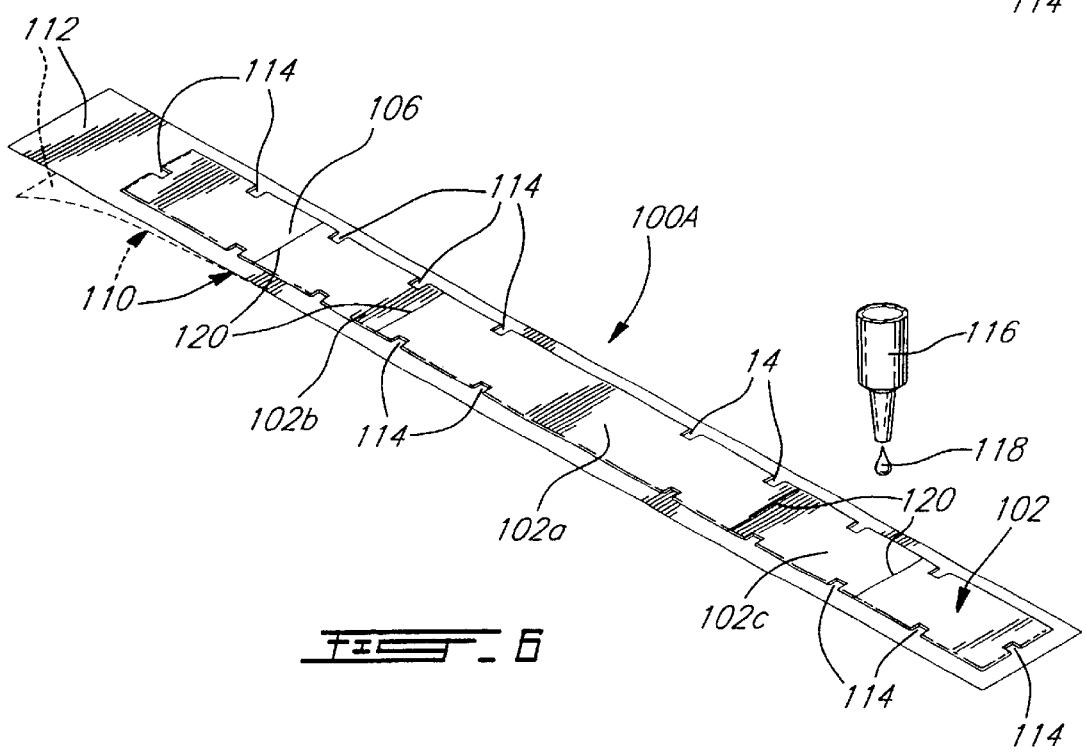

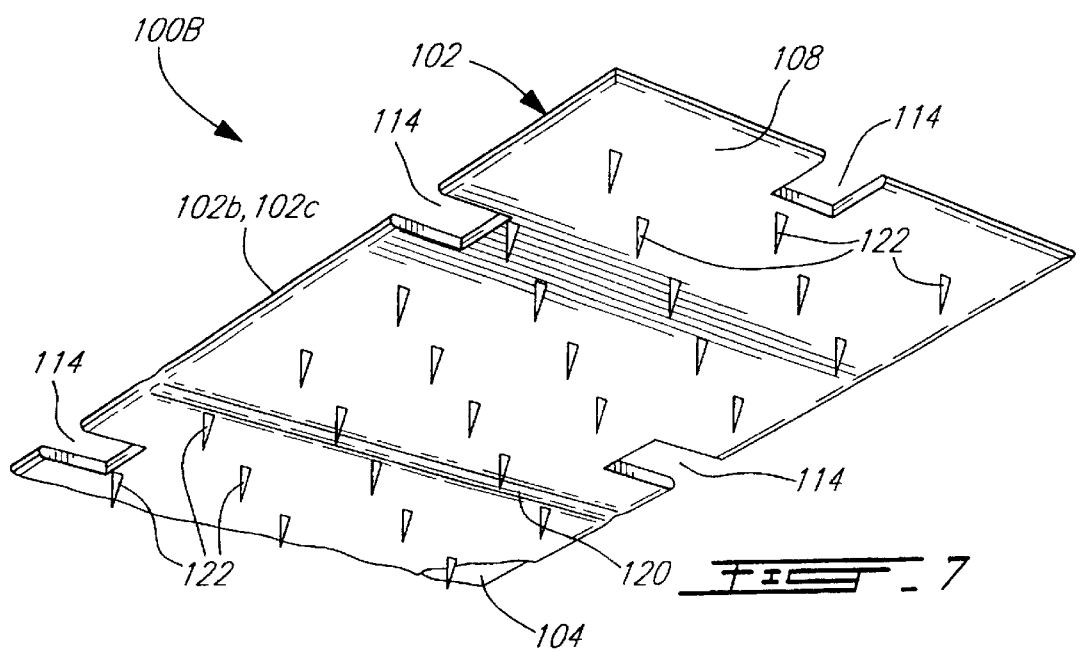
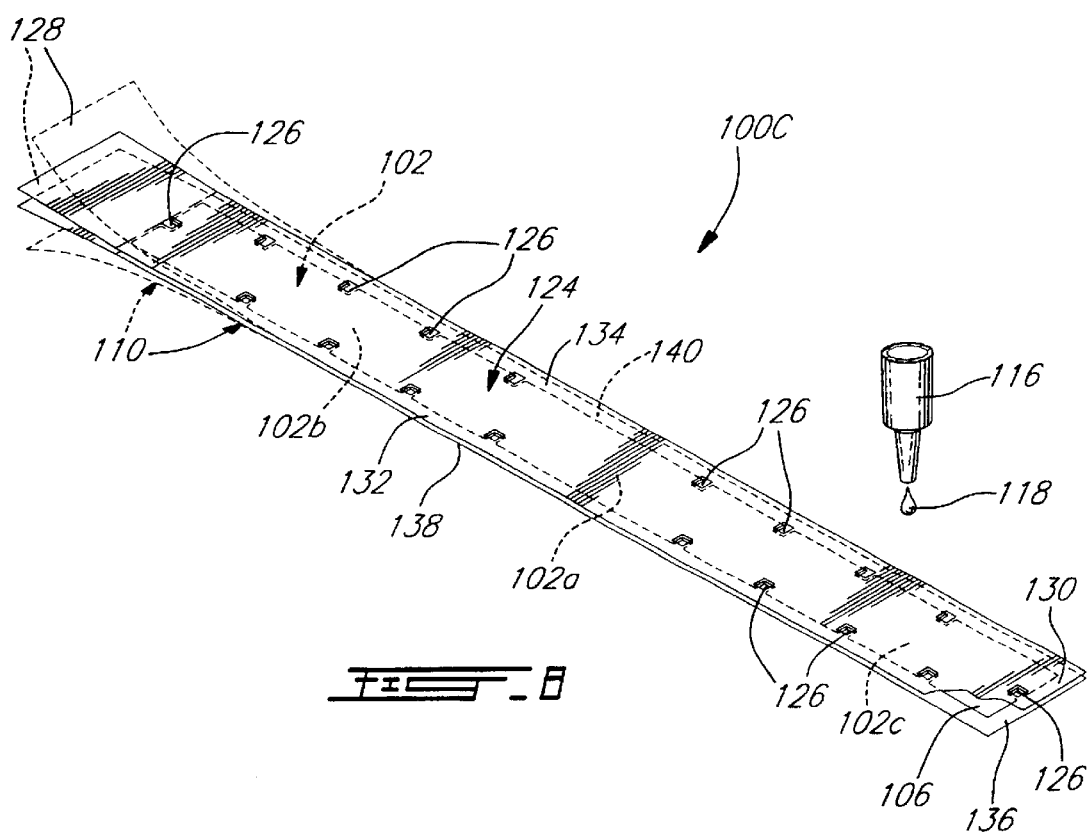

WOUND CLOSURE SYSTEM

TECHNICAL FIELD

The present invention pertains to improvements in the field of wound care. More particularly, the invention relates to a wound closure system for closing a wound on a patient.

BACKGROUND ART

When closing a wound, it is necessary to join and keep together the facing edges of the wound. If the separated skin sections are sewn, unesthetical scars may remain, and if they are stapled, such scars generally remain.

Cyanoacrylate-based adhesives have been suggested as an alternative to sutures. When a cyanoacrylate adhesive is employed, the separated skin sections are joined and the adhesive is applied on top of the joined sections under sterile conditions. The cyanoacrylate adhesive bonds to the skin and polymerizes so as to keep together the joined sections. Although cyanoacrylate adhesives successfully bind the skin, the use of such adhesives as suture replacements can be accompanied by occasional adhesion failure resulting in wound reopening which requires closure by sutures. Fear of wound reopening is one of the reasons physicians have been reluctant to use any adhesive including cyanoacrylate based adhesives instead of sutures.

U.S. Pat. No. 5,254,132 proposes a method of treating suturable wounds by first suturing or stapling the wound and then joining the skin between sutures or staples with a cyanoacrylate adhesive. According to this method, the wound is sutured or stapled so that the sutures or staples are separated from each other by no more than about 1.2 centimeter and no less than about 0.6 centimeter. Butyl 2-cyanoacrylate is then applied to the opposing and still separated skin sections between the sutures or staples in an amount sufficient so that upon polymerization the skin sections are joined; the application is conducted so that contact of the cyanoacrylate adhesive with the sutures or staples is avoided. The adjacent separated skin sections are thereafter contacted under conditions that permit the adhesive to polymerize so as to join the separated skin sections. Such a method is not only time-consuming and requires particular skill to practice, but also delays healing of the wound if cyanoacrylate adhesive penetrates in between the skin sections.

Surgical adhesive strips for closing wounds are also known. These strips generally do not have much tensile strength so that their use is limited to shallow wounds requiring little tension to close. Another major disadvantage resides in their permeability to water, causing the strips to become unstuck upon contact with water or moisture and thereby preventing the wounded area from being washed.

U.S. Pat. No. 5,259,835 discloses a wound closure device that employs a porous bonding member adapted to receive a flowable moisture-curable surgical adhesive. The bonding member is positioned by a carrier member which is used to achieve initial apposition of the wound and which may later be removed. Since the adhesive flows into the bonding member and the latter serves as a matrix for the adhesive, the bonding member becomes rigid as the adhesive therein undergoes curing so that it looses flexibility. Part of the surgical adhesive also flows through the bonding member and may enter into the wound.

DISCLOSURE OF THE INVENTION

It is therefore an object of the present invention to overcome the above drawbacks and to provide a wound closure system for closing wounds.

In accordance with the invention, there is provided a wound closure system for closing a wound on a patient, comprising:

an elongated, flexible backing strip having opposite ends, first and second surfaces facing away from one another and a length and width sufficient to secure facing edges of the wound in close juxtaposition to one another, the backing strip comprising a first portion disposed between the ends and adapted to overlie the facing edges of the wound, and second and third portions disposed on either side of the first portion and each provided with a predetermined number of spaced-apart apertures extending through the backing strip from one surface thereof to the other, the first portion being free of any such aperture;

a first pressure-sensitive adhesive coated on at least part of the first surface of the backing strip including the second and third portions thereof, to adhere at least the second and third portions of the, backing strip to the patient with the facing edges of the wound being in close juxtaposition;

a first protective member removably attached to the backing strip and covering the pressure-sensitive adhesive; and a flowable, moisture-curable surgical adhesive for application into the apertures to strengthen the adhesion of the second and third portions of the backing strip to the patient.

After removal of the protective member to expose the pressure-sensitive adhesive, application of the backing strip with the exposed pressure-sensitive adhesive onto the patient to secure the facing edges of the wound in close juxtaposition and application of the surgical adhesive into the apertures, the surgical adhesive flows through the apertures and upon curing forms discrete bonding sites cooperating with the backing strip to maintain the facing edges of the wound in close juxtaposition without the cured adhesive adversely affecting the flexibility of the backing strip.

Applicant has found quite unexpectedly that by using a flexible backing strip having a non-perforated first portion disposed between the ends thereof and perforated second and third portions disposed on either side of the first portions, and a pressure-sensitive adhesive coated on at least part of the first surface of the backing strip including the second and third portions thereof, and applying a flowable, moisture-curable surgical adhesive into the apertures or perforations defined in the second and third portions, after application of the backing strip with the exposed pressure-sensitive adhesive onto the patient to secure the facing edges of the wound in close juxtaposition, the surgical adhesive flows through the apertures and upon curing forms discrete bonding sites strengthening the adhesion of the second and third portions of the backing strip to the patient and cooperating with the backing strip to maintain the facing edges of the wound in close juxtaposition without the cured adhesive adversely affecting the flexibility of the backing strip. Since the surgical adhesive is applied on either side of the first portion of the backing strip which overlies the facing edges of the wound, the surgical adhesive does not enter into the wound so that healing of the wound is not delayed. On the other hand, since the flexibility of the backing strip is not adversely affected by the cured adhesive, the strip remains flexible and can thus follow movements of the skin.

Preferably, the backing strip comprises a sheet of polymer such as polyurethane or nylon. It can also comprise a web of fabric material such as cotton, rayon, acrylic or polyester fibers. The protective member, on the other hand, preferably comprises a film of high density polyethylene or a sheet of wax paper.

According to a preferred embodiment of the invention, the apertures are perforations having a circular cross-section with a diameter ranging from 0.5 to 3 mm, preferably from 1 to 2 mm. For a backing strip with the first or second surface thereof defining an area of about 12 cm, the number of perforations defined in each of the second and third portions can vary between 4 and 20, and preferably ranges from 8 to 12. Preferably, a second protective member having a second pressure-sensitive adhesive coated on one side thereof is removably attached to the backing strip and covers the second surface thereof, the strip being disposed between the first and second protective members. The second protective member is provided with a corresponding number of perforations registering with the perforations defined in the second and third portions of the backing strip, and being in flow communication therewith. The provision of such a second protective member prevents the surgical adhesive from contacting the second surface of the backing strip during its application so that when the second protective member together with the second pressure-sensitive adhesive are removed from the backing strip following application of the surgical adhesive, there is no surgical adhesive on the second surface, which upon curing could adversely affect the flexibility of the backing strip. The second protective member preferably comprises a film of low density polyethylene. Instead of using a second pressure-sensitive adhesive, it is also possible to removably attach the second protective member to the backing strip by heat or pressure application.

According to another preferred embodiment, the second and third portions of the backing strip each have an end edge and a pair of opposite side edges, and the apertures are U-shaped notches defined along the side and end edges of each of the second and third portions. Preferably, a removable second protective member similar to the one described above, but having perforations registering with the notches and being in flow communication therewith, covers the second surface of the backing strip.

According to a further preferred embodiment, the second and third portions of the backing strip are each provided with at least one fold line extending transversely of the strip between the apertures to increase the flexibility of the backing strip.

According to yet another preferred embodiment, the second and third portions of the backing strip are each provided with a plurality of spaced-apart anchoring elements disposed between the apertures and projecting outwardly from the first surface. These anchoring elements assist in securing the facing edges of the wound in close juxtaposition.

BRIEF DESCRIPTION OF DRAWINGS

Further features and advantages of the present invention will become more readily apparent from the following description of preferred embodiments as illustrated by way of examples in the accompanying drawings, in which:

FIG. 1 is a top perspective view of a wound closure system according to a preferred embodiment of the invention;

FIG. 2 is a top perspective view of a wound closure system similar to that illustrated in FIG. 1, but with the backing strip provided with a plurality of spaced-apart transversely extending fold lines;

FIG. 3 is a fragmentary bottom perspective view of a wound closure system similar to that illustrated in FIG. 2, but with the backing strip provided with a plurality of spaced-apart downwardly extending anchoring elements;

FIG. 4 is a top perspective view of a wound closure system similar to that illustrated in FIG. 1, but with the backing strip provided with a second protective member;

FIG. 5 is a top perspective view of a wound closure system according to another preferred embodiment of the invention;

FIG. 6 is a top perspective view of a wound closure system similar to that illustrated in FIG. 5, but with the backing strip provided with a plurality of spaced-apart transversely extending fold lines;

FIG. 7 is a fragmentary bottom perspective view of a wound closure system similar to that illustrated in FIG. 6, but with the backing strip provided with a plurality of spaced-apart downwardly extending anchoring elements; and FIG. 8 is a top perspective view of a wound closure system similar to that illustrated in FIG. 5, but with the backing strip provided with a second protective member.

MODES FOR CARRYING OUT THE INVENTION

Referring first to FIG. 1, there is illustrated a wound closure system which is generally designated by reference numeral 10 and used for closing a wound on a patient (not shown). The wound closure system 10 comprises an elongated flexible backing strip 12 having surfaces 14 and 16 facing away from one another with the surface 14 being coated with a pressure-sensitive adhesive 18. The backing strip 12 has a length and width sufficient to secure facing edges of the wound in close juxtaposition to one another. A protective member 20 is removably attached to the backing strip 12 and covers the adhesive 18. The protective member 20 extends beyond an end edge of the backing strip 12 to define a finger-grip tab 22. The backing strip 12 has a substantially central portion 12a adapted to overlie the facing edges of the wound, and two portions 12b, 12c disposed on either side of portion 12a and each provided with a predetermined number of spaced-apart circular perforations 24 extending through the backing strip from one surface to the other.

The wound closure system 10 further includes a source 26 of flowable, moisture-curable surgical adhesive 28 for application into the perforations 24. Examples of suitable surgical adhesives which can be used include cyanoacrylates such as n-butyl 2-cyanoacrylate and octyl 2-cyanoacrylate.

In use, the protective member 20 is first peeled-off to expose the pressure-sensitive adhesive 18 and one of the portions 12b,12c of the backing strip 12 with the exposed adhesive 18 is adhered to one of the separated skin sections, which is then pulled in a direction towards the other separated skin section to bring the facing edges of the wound in close juxtaposition to one another, and the other portion of the strip 12 is adhered to the other skin section, thereby closing the wound and securing the facing edges thereof in close juxtaposition. The surgical adhesive 28 is then applied into the perforations 24 defined in the portions 12b,12c of the backing strip 12 to strengthen the adhesion of the portions 12b and 12c to the patient's skin. The adhesive 28 flows through the perforations 24 and upon curing forms discrete bonding sites cooperating with the strip 12 to maintain the facing edges of the wound in close juxtaposition without the cured adhesive adversely affecting the flexibility of the strip 12.

The wound closure system 10A illustrated in FIG. 2 is similar to the one shown in FIG. 1, with the exception that the backing strip is provided with a plurality of spaced-apart transversely extending fold lines to increase the flexibility of the strip 12. As shown, the fold lines 30 extend between the perforations 24.

The wound closure system 10B which is partially illustrated in FIG. 3 is similar to the one shown in FIG. 2, with the exception that each of the portions 12b,12c of the backing strip 12 is provided with a plurality of spaced-apart hook-shaped elements 32 disposed between the perforations 24 and projecting outwardly from the surface 14. The anchoring elements 32 assist in securing the facing edges of the wound in close juxtaposition.

The wound closure system 10C illustrated in FIG. 4 is similar to the one shown in FIG. 1, with the exception that a second protective member 34 having a pressure-sensitive adhesive (not shown) coated on one side thereof is removably attached to the backing strip 12, and covers the surface 16, the strip 12 being disposed between the protective members 20 and 34. The protective member 34 is provided with perforations 36 whose number is the same as the number of perforations 24 defined in the portions 12b,12c of the strip 12. The perforations 36 register with the perforations 24 and are in flow communication therewith. The protective member 34 extends beyond an end edge of the backing strip to define a finger-grip tab 38 which is free of adhesive. The provision of such a protective member 34 prevents the surgical adhesive 28 from contacting the surface 16 of the backing strip during its application so that when the protective member 34 together with the pressure-sensitive adhesive coated thereon are removed from the backing strip 12 following application of the surgical adhesive 28, there is no surgical adhesive 28 on the surface 16, which upon curing could adversely affect the flexibility of the backing strip 12.

Turning to FIG. 5, there is illustrated another wound closure system which is generally designated by reference numeral 100 and comprises an elongated flexible backing strip 102 having surfaces 104 (shown in FIG. 7) and 106 facing away from one another with the surface 104 being coated with a pressure-sensitive adhesive 108 (shown in FIG. 7). The backing strip has a length and width sufficient to secure facing edges of a wound (not shown) in close juxtaposition to one another. A protective member 110 is removably attached to the backing strip and covers the adhesive 108. The protective member 110 extends beyond an end edge of the backing strip 102 to define a finger-grip tab 112. The backing strip has a substantially central portion 102a adapted to overlie the facing edges of the wound, and two portions 102b,102c disposed on either side of portion 102a. A plurality of spaced-apart generally U-shaped notches 114 are defined along the side and end edges of each of the portions 102b,102c.

The wound closure system 100 further includes a source 116 of flowable, moisture curable adhesive 118 which is the same as the adhesive 28 shown in FIGS. 1–4, for application into the notches 114. It is used in the same manner as the wound closure system 10 shown in FIG. 1 to close a wound.

The wound closure system 100A illustrated in FIG. 6 is similar to the one shown in FIG. 5, with the exception that the backing strip 102 is provided with a plurality of spaced-apart transversely extending fold lines 120 to increase the flexibility of the strip 102. As shown, the fold lines 120 extend between the notches 114.

The wound closure system 100B which is partially illustrated in FIG. 7 is similar to the one shown in FIG. 6, with the exception that each of the portions 102b,102c of the backing strip 102 is provided with a plurality of spaced-apart hook-shaped anchoring elements 122 projecting outwardly from the surface 104. The anchoring elements 122 serve the same purpose as the anchoring elements 32 shown in FIG. 3.

The wound closure system 100C illustrated in FIG. 8 is similar to the one shown in FIG. 5, with the exception that a second protective member 124 having a pressure-sensitive adhesive (not shown) coated on one side thereof is removably attached to the backing strip 102 and covers the surface 106, the strip 102 being disposed between the protective members 110 and 124. The protective member 124 is provided with square perforations 126 whose number is the same as the number of notches 114. The perforations 126 register with the notches 114 and are in flow communication therewith. The protective member 124 extends beyond one of the end edges of the backing strip 102 to define a finger-grip tab 128 which is free of adhesive. The protective member 124 also extends beyond the other end edge of the strip 102 and side edges thereof to define an end portion 130 and lateral portions 132,134. Similarly, the protective member 110 extends beyond the other end edge of the strip 102 and side edges thereof to define an end portion 136 and lateral portions 138,140. The end portions 130,136 and lateral portions 132,138 and 134,140 face one another and are releasably bonded together by the adhesive coated on the protective member 124. The member 124 serves the same-;purpose as the member 34 shown in FIG. 4. It also serves to confine the surgical adhesive 118 in the notches 114 during curing of the adhesive 118.

What is claimed is:

1. A wound closure system for closing a wound on a patient, comprising:

an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart perforations extending through said backing strip from said first surface to said second surface, said first portion being free of any aperture extending through said backing strip from said first surface to said second surface;

a first pressure-sensitive adhesive coated on at least part of the first surface of said backing strip including said second and third portions thereof, to adhere at least said second and third portions of said backing strip to the patient with the facing edges of said wound in said close juxtaposition;

a first protective member removably attached to said backing strip and covering said pressure-sensitive adhesive; and a flowable, moisture-curable surgical adhesive for application into said perforations to strengthen the adhesion of said second and third portions of said backing strip to the patient;

whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said perforations and upon curing forms discrete bonding sites cooperating with said backing strip to maintain the facing edges of said wound in said close juxtaposition without the cured adhesive adversely affecting the flexibility of said backing strip, wherein a second protective member having a second pressure-sensitive adhesive coated on one side thereof is removably attached to said backing strip and covers said second surface, said strip being disposed between said first and second protective members, and wherein said second protective member is provided with a corresponding number of perforations registering with the perforations defined in said second and third portions of said backing strip, and being in flow communication therewith.

2. A wound closure system according to claim 1, wherein said backing strip comprises a web of fabric material.

3. A wound closure system according to claim 1, wherein said backing strip comprises a sheet of polymer selected from the group consisting of polyurethane and nylon.

4. A wound closure system according to claim 1, wherein said perforations have a circular cross-section with a diameter ranging from 0.5 to 3 mm.

5. A wound closure system according to claim 4, wherein said perforations have a diameter between 1 and 2 mm.

6. A wound closure system according to claim 4, wherein the number of perforations defined in each of said second and third portions ranges from 4 to 20 when the first or second surface of said backing strip has an area of about 12 cm$^2$.

7. A wound closure system according to claim 6, wherein the number of perforations is between 8 and 12.

8. A wound closure system for closing a wound on a patient, comprising:

an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart perforations extending through said backing strip from said first surface to said second surface, said first portion being free of any aperture extending through said backing strip from said first surface to said second surface;

a first pressure-sensitive adhesive coated on at least part of the first surface of said backing strip including said second and third portions thereof, to adhere at least said second and third portions of said backing strip to the patient with the facing edges of said wound in said close juxtaposition;

a first protective member removably attached to said backing strip and covering said pressure-sensitive adhesive; and a flowable, moisture-curable surgical adhesive for application into said perforations to strengthen the adhesion of said second and third portions of said backing strip to the patient;

whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said perforations, said surgical adhesive flows through said perforations and upon curing forms discrete bonding sites cooperating with said backing strip to maintain the facing edges of said wound in said close juxtaposition without the cured adhesive adversely affecting the flexibility of said backing strip, wherein a second protective member is removably attached to said backing strip by heat or pressure application and covers said second surface, said strip being disposed between said first and second protective members, and wherein said second protective member is provided with a corresponding number of perforations registering with the perforations defined in said second and third portions, and being in flow communication therewith.

9. A wound closure system for closing a wound on a patient, comprising:

an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart apertures extending through said backing strip from said first surface to said second surface, said first portion being free of any aperture extending through said backing strip from said first surface to said second surface;

a first pressure-sensitive adhesive coated on at least part of the first surface of said backing strip including said second and third portions thereof, to adhere at least said second and third portions of said backing strip to the patient with the facing edges of said wound in said close juxtaposition, and wherein said second and third portions of said backing strip each have an end edge and a pair of opposite side edges, and wherein said apertures are notches defined along the side and end edges of each of said second and third portions;

a first protective member removably attached to said backing strip and covering said pressure-sensitive adhesive; and a flowable, moisture-curable surgical adhesive for application into said apertures to strengthen the adhesion of said second and third portions of said backing strip to the patient;

whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said apertures and upon curing forms discrete bonding sites cooperating with said backing strip to maintain the facing edges of said wound in said close juxtaposition without the cured adhesive adversely affecting the flexibility of said backing strip, wherein a second protective member having a second pressure-sensitive adhesive coated on one side thereof is removably attached to said backing strip and covers said second surface, said strip being disposed between said first and second protective members, and wherein said second protective member is provided with a corresponding number of apertures registering with said notches and being in flow communication therewith.

10. A wound closure system for closing a wound on a patient, comprising:

an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart apertures extending through said backing strip from said first surface to said second surface, said first portion being free of any aperture extending through said backing strip from said first surface to said second surface;

a first pressure-sensitive adhesive coated on at least part of the first surface of said backing strip including said second and third portions thereof, to adhere at least said second and third portions of said backing strip to the patient with the facing edges of said wound in said close juxtaposition, and wherein said second and third portions of said backing strip each have an end edge and a pair of opposite side edges, and wherein said apertures are notches defined along the side and end edges of each of said second and third portions;

a first protective member removably attached to said backing strip and covering said pressure-sensitive adhesive; and a flowable, moisture-curable surgical adhesive for application into said apertures to strengthen the adhesion of said second and third portions of said backing strip to the patient;

whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said apertures and upon curing forms discrete bonding sites cooperating with said backing strip to maintain the facing edges of said wound in said close juxtaposition without the cured adhesive adversely affecting the flexibility of said backing strip, wherein a second protective member is removably attached to said backing strip by heat or pressure application and covers said second surface, said strip being disposed between said first and second protective members, and wherein said second protective member is provided with a corresponding number of apertures registering with said notches and being in flow communication therewith.

11. A wound closure system according to claim 9 or 10, wherein said notches are U-shaped.

12. A wound closure system according to claim 1, 8, 9 or 10, wherein said second protective member comprises a film of low density polyethylene.

13. A wound closure system according to claim 1, 8, 9 or 10, wherein said first protective member comprises a film of high density polyethylene or a sheet of wax paper.

14. A wound closure system according to claim 1, 8, 9 or 10, wherein said second and third portions of said backing strip are each provided with at least one fold line extending transversely of said strip between said apertures to increase the flexibility of said backing strip.

15. A wound closure system according to claim 1, 8, 9 or 10, wherein said second and third portions of said backing strip are each provided with a plurality of spaced-apart anchoring elements disposed between said apertures and projecting outwardly from said first surface.

16. A wound closure system according to claim 15, wherein said anchoring elements are hook-shaped.

17. A wound closure system according to claim 1, 8, 9 or 10, wherein said surgical adhesive comprises a cyanoacrylate.

18. A wound closure system according to claim 17, wherein said cyanoacrylate is n-butyl 2-cyanoacrylate or octyl 2-cyanoacrylate.

19. A method for closing a wound on a patient, comprising:

(a.) providing a flexible closure system comprising:

an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart apertures extending through said backing strip from said first surface to said second surface, said first portion being free of any aperture extending through said backing strip from said first surface to said second surface, said first portion being free of any aperture extending through said backing strip from said first surface to said second surface;

a first pressure-sensitive adhesive coated on at least part of the first surface of said backing strip including said second and third portions thereof, to adhere at least said second and third portions of said backing strip to the patient with the facing edges of said wound in said close juxtaposition;

a first protective member removably attached to said backing strip and covering said pressure-sensitive adhesive; and a flowable, moisture-curable surgical adhesive for application into said apertures to strengthen the adhesion of said second and third portions of said backing strip to the patient;

(b.) removing of said protective member to expose said pressure-sensitive adhesive;

(c.) applying said backing strip with the exposed pressure-sensitive adhesive onto said patient to secure the facing edges of said wound in close juxtaposition; and (d.) applying said surgical adhesive into said apertures such that said surgical adhesive flows through said apertures and upon curing forms discrete bonding sites cooperating with said backing strip to maintain the facing edges of said wound in said close juxtaposition, whereby the cured adhesive does not adversely affect the flexibility of said backing strip.

* * * * *